US009498651B2

(12) United States Patent
Sapozhnikov et al.

(10) Patent No.: US 9,498,651 B2
(45) Date of Patent: Nov. 22, 2016

(54) METHODS OF SOFT TISSUE EMULSIFICATION USING A MECHANISM OF ULTRASONIC ATOMIZATION INSIDE GAS OR VAPOR CAVITIES AND ASSOCIATED SYSTEMS AND DEVICES

(75) Inventors: Oleg A. Sapozhnikov, Seattle, WA (US); Michael R. Bailey, Seattle, WA (US); Lawrence A. Crum, Bellevue, WA (US); Tatiana D. Khokhlova, Seattle, WA (US); Vera A. Khokhlova, Seattle, WA (US); Julianna C. Simon, Kenmore, WA (US); Yak-Nam Wang, Seattle, WA (US)

(73) Assignee: University of Washington, Seattle, WA (US)

( * ) Notice: Subject to any disclaimer, the term of this patent is extended or adjusted under 35 U.S.C. 154(b) by 1114 days.

(21) Appl. No.: 13/444,466

(22) Filed: Apr. 11, 2012

(65) Prior Publication Data

US 2012/0259250 A1 Oct. 11, 2012

Related U.S. Application Data

(60) Provisional application No. 61/474,080, filed on Apr. 11, 2011, provisional application No. 61/488,552, filed on May 20, 2011.

(51) Int. Cl.
*A61B 8/00* (2006.01)
*A61N 7/02* (2006.01)
*A61N 7/00* (2006.01)

(52) U.S. Cl.
CPC . *A61N 7/02* (2013.01); *A61B 8/00* (2013.01); *A61N 2007/0039* (2013.01)

(58) Field of Classification Search
CPC ... A61N 2007/0039; A61N 7/02; A61B 8/00
USPC ........................................................ 601/2, 4
See application file for complete search history.

(56) References Cited

U.S. PATENT DOCUMENTS 6,695,781 B2 2/2004 Rabiner et al.
2003/0229331 A1* 12/2003 Brisken et al. ............... 604/500

(Continued)

FOREIGN PATENT DOCUMENTS

WO WO-2010118539 A2 10/2010

OTHER PUBLICATIONS

Julianna C. Simon, Oleg A. Sapozhnikov, Vera A. Khokhlova, Yak-Nam Wang, Lawrence A. Crum, Michael R. Bailey. "Ultrasonic atomization of tissue and its role in tissue fractionation by high intensity focused ultrasound." Phys Med Biol. Dec. 7, 2012; 57(23): 8061-8078.*

(Continued)

*Primary Examiner* — Amanda Lauritzen Moher
(74) *Attorney, Agent, or Firm* — Perkins Coie LLP

(57) ABSTRACT

The present technology is directed to methods of soft tissue emulsification using a mechanism of ultrasonic atomization inside gas or vapor cavities, and associated systems and devices. In several embodiments, for example, a method of non-invasively treating tissue includes pulsing ultrasound energy from the ultrasound source toward the target site in tissue. The ultrasound source is configured to emit high intensity focused ultrasound (HIFU) waves. The target site comprises a pressure-release interface of a gas or vapor cavity located within the tissue. The method continues by generating shock waves in the tissue to induce a lesion in the tissue at the target site. The method additionally includes characterizing the lesion based on a degree of at least one of a mechanical or thermal ablation of the tissue.

15 Claims, 5 Drawing Sheets

(56) References Cited

U.S. PATENT DOCUMENTS

| | | | | |
|---|---|---|---|---|
| 2008/0269163 | A1 | 10/2008 | Sostaric et al. | |
| 2008/0269668 | A1 | 10/2008 | Keenan et al. | |
| 2008/0319356 | A1* | 12/2008 | Cain et al. | 601/2 |
| 2009/0177085 | A1 | 7/2009 | Maxwell et al. | |
| 2010/0228122 | A1 | 9/2010 | Keenan et al. | |
| 2011/0054363 | A1 | 3/2011 | Cain | |
| 2011/0251528 | A1 | 10/2011 | Canney et al. | |
| 2011/0257523 | A1 | 10/2011 | Hastings | |
| 2012/0010541 | A1 | 1/2012 | Cain | |
| 2013/0230930 | A2* | 9/2013 | VanDoorn | G01N 1/44 436/174 |
| 2014/0243664 | A1* | 8/2014 | El-Sayed | A61K 49/22 600/431 |

OTHER PUBLICATIONS

Yak-Nam Wang, Tatiana Khokhlova, Michael Bailey, Joo Ha Hwang, and Vera Khokhlova. "Histological and biochemical analysis of mechanical and thermal bioeffects in boiling histotripsy lesions induced by high intensity focused ultrasound." Ultrasound Med Biol. Mar. 2013;39(3):424-38.*

Simon JC et al. "Ultrasonic atomization of liquids in drop-chain acoustic fountains." J Fluid Mech. Mar. 2015; 766: 129-146.*

Simon JC et al. "Ultrasonic atomization of tissue and its role in tissue fractionation by high intensity focused ultrasound." Phys Med Biol. Dec. 7, 2012; 57(23): 8061-78.*

JC Simon et al. "Ultrasonic atomization of liquids in drop-chain acoustic fountains." J Fluid Mech. Mar. 2015; 766: 129-146.*

J Simon et al. "Miniature acoustic fountain mechanism for tissue emulsification during millisecond boiling in high intensity focused ultrasound fields." J. Acoust. Soc. Am. 129, 2478 (2011). Abstract only.*

O Sapozhnikov et al. "Ultrasonic atomization on the tissue—bubble interface as a possible mechanism of tissue erosion in histotripsy." J. Acoust. Soc. Am. 129, 2478 (2011). Abstract only.*

J Simon et al. "Tissue atomization by high intensity focused ultrasound." 2012 IEEE International Ultrasonics Symposium: pp. 1003-1006. Conference dates Oct. 7-10, 2012.*

Canney et al., "Shock-Induced Heating and Millisecond Boiling in Gels and Tissue Due to High Intensity Focused Ultrasound", Ultrasound in Medicine & Biology, vol. 36, No. 2 (2010), pp. 250-267.

Xu et al., "High Speed Imaging of Bubble Clouds Generated in Pulsed Ultrasound Cavitational Therapy—Histotripsy", IEEE Trans Ultrason Ferroelectr Freq Control, vol. 54, No. 10 (Oct. 2007), pp. 2091-2101.

* cited by examiner

METHODS OF SOFT TISSUE EMULSIFICATION USING A MECHANISM OF ULTRASONIC ATOMIZATION INSIDE GAS OR VAPOR CAVITIES AND ASSOCIATED SYSTEMS AND DEVICES

CROSS-REFERENCE TO RELATED APPLICATIONS

This application claims the benefit of U.S. Provisional Application No. 61/474,080, filed Apr. 11, 2011, and U.S. Provisional Application No. 61/488,552, filed May 20, 2011, both of which are incorporated herein by reference in their entireties.

STATEMENT REGARDING FEDERALLY SPONSORED RESEARCH

This invention was made with government support under 1R01EB007643-01A2 awarded by National Institutes of Health (NIH) and SMST01601 (NASA NCC 9-58) awarded by National Space Biomedical Research Institute (NSBRI). The government has certain rights in the invention.

TECHNICAL FIELD

The present technology relates generally to high intensity focused ultrasound. In particular, several embodiments are directed toward methods and systems for non-invasive treatment of tissue using high intensity focused ultrasound therapy.

BACKGROUND

Minimally invasive and non-invasive therapeutic ultrasound treatments can be used to ablate, necrotize, and/or otherwise damage tissue. High intensity focused ultrasound ("HIFU"), for example, is used to thermally or mechanically damage tissue. HIFU thermal treatments increase the temperature of tissue at a focal region such that the tissue quickly forms a thermally coagulated treatment volume. HIFU treatments can also cause mechanical disruption of tissue with well-demarcated regions of mechanically emulsified treatment volumes that have little remaining cellular integrity. For certain medical applications, tissue emulsification may be more favorable than thermal damage because it produces liquefied volumes that can be more easily removed or absorbed by the body than thermally coagulated solid volumes.

HIFU treatments can utilize a sequence of pulses, rather than continuous-wave HIFU exposures, to reduce undesirable thermal effects on the surrounding tissue. In histotripsy exposures, for example, HIFU sources operate with low duty cycles (e.g., 1%), use relatively short pulses (e.g., 10-20 microseconds), and deliver high pulse average intensities of up to 40 $kW/cm^2$ to form bubbles that mechanically disrupt tissue. Histotripsy techniques, for example, can induce cavitation by delivering pulses of high peak negative pressures that are significantly higher than the tensile strength of the tissue. The repetition of such pulses can increase the area of tissue affected by cavitation to create a "cavitation cloud" that emulsifies the tissue. Cavitation, however, is generally stochastic in nature, making cavitation-based HIFU treatments somewhat unpredictable and difficult to reproduce. Therefore, there is a need to enhance the reliability, predictability, and repeatability of mechanical disruption of tissue damage (e.g., emulsification).

DETAILED DESCRIPTION

The present technology is directed to methods of soft tissue emulsification using a mechanism of ultrasonic atomization inside gas or vapor cavities, and associated systems and devices. In several embodiments, for example, a method of non-invasively treating tissue includes pulsing ultrasound energy from the ultrasound source toward the target site in tissue. The ultrasound source is configured to emit HIFU waves. The target site comprises a pressure-release interface of a gas or vapor cavity located within the tissue. The method continues by generating shock waves in the tissue to induce a lesion in the tissue at the target site. The method additionally includes characterizing the lesion based on a degree of at least one of a mechanical or thermal ablation of the tissue. These HIFU systems and methods have a number of both therapeutic and cosmetic applications, such as producing bulk ablation of benign and malignant tumors.

Certain specific details are set forth in the following description and in FIGS. 1-5 to provide a thorough understanding of various embodiments of the technology. For example, several embodiments of HIFU treatments that destroy tissue are described in detail below. The present technology, however, may be used to destroy multi-cell structures similar to tissue. Additionally, the term "target site" is used broadly throughout the disclosure to refer to any volume or region of tissue that may benefit from HIFU treatment. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-5.

Figure 1:
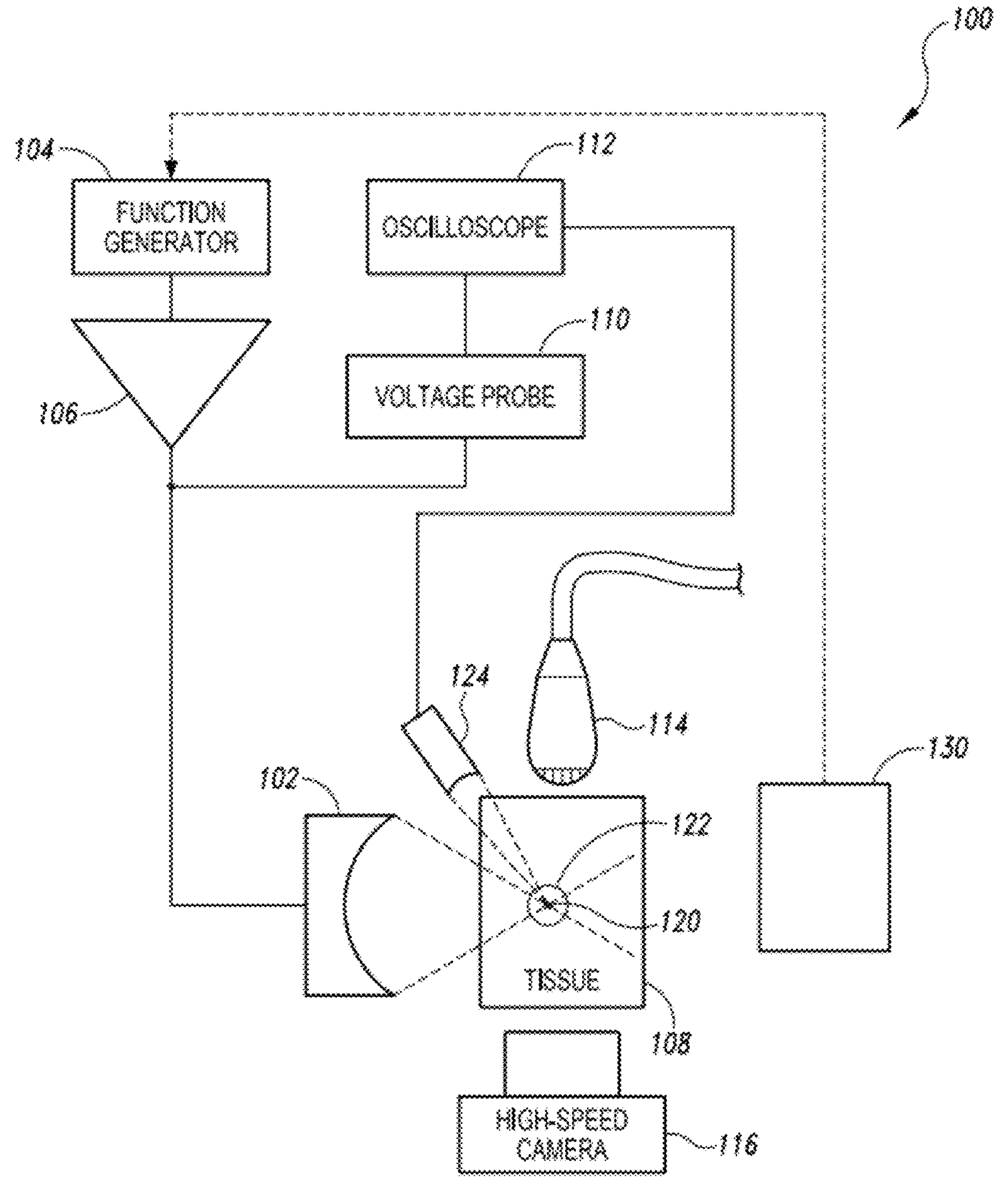
FIG. 1 is a schematic view of a HIFU system configured in accordance with an embodiment of the present technology.

FIG. 1 is a schematic view of a HIFU system 100 configured in accordance with an embodiment of the present technology. The HIFU system 100 can include a HIFU source 102 operably coupled to a function generator 104 and an amplifier 106. The HIFU source 102 can be an ultrasound transducer that emits high levels of ultrasound energy to a focus 120. The focus 120 can be a point, plane, or region at which the intensity from the HIFU source 102 is the highest. In other embodiments, the HIFU source 102 can include a single-element device, a multi-element device, an extracorporeal device, an intracavitary device, and/or other devices or systems configured to emit HIFU energy to a focus. The HIFU source 102 can have a frequency range of approximately 0.5-20 MHz. In other embodiments, the frequency of the HIFU source 102 can vary. The function generator 104 (e.g., an Agilent 33250A function generator from Agilent of Palo Alto, Calif.) and the amplifier 106 (e.g., an ENI A-300 300 W RF amplifier from ENI of Rochester, N.Y.) can drive the HIFU source 102 to generate pulsed shock waves proximate to the focus 120. Accordingly, the HIFU system 100 can implement a pulsing protocol in which ultrasound frequency, pulse repetition frequency, pulse length, duty cycle, pressure amplitude, and/or other factors associated with the HIFU treatment can be adjusted to generate shock waves proximate to the focus 120.

During treatment the HIFU source 102 can be positioned proximate to tissue 108, and the focus 120 of the HIFU source 102 can be aligned with at least a portion of a target site 122 within the tissue 108. For example, the HIFU source 102 can be positioned over a patient's kidney, heart, or liver, and the focus 120 can be aligned with infected or otherwise adverse tissue therein. In still other embodiments, a variety of other types of tissue may be treated using the HIFU system 100. Larger target sites 122 can be mechanically fractionated by scanning the HIFU source 102 over the treatment region using either mechanical or electronic scanning. Such scanning and the initial positioning of the HIFU source 102 can be performed manually or mechanically (e.g., using a three-axis positioning system, not shown). The function generator 104 can initiate the pulsing protocol to generate shock waves with amplitudes between approximately 10 MPa and approximately 80 MPa at the focus 120 with the HIFU source 102 having a frequency of approximately 2 MHz. In other embodiments, such as at lower or higher ultrasound frequencies, the shock wave amplitudes of the HIFU source 102 can be greater or smaller. Absorption of ultrasonic energy occurs primarily at the shock front and induces heating of the tissue 108 that can exceed boiling temperature in the tissue 108.

During each HIFU pulse, one or more boiling bubbles can be formed in the tissue. In several embodiments, for example, the boiling bubbles can have cross-sectional dimensions of approximately 2-4 mm when the ultrasound frequency is approximately 2 MHz. In other embodiments, however, the boiling bubbles can be larger or smaller. For example, the boiling bubbles in the tissue can have a cross-sectional dimension between approximately 100 μm and approximately 4 mm on the order of the beam-width of the ultrasound source 102 at the focus 120. The superheated vapor of the boiling bubbles provides a force pushing outward from the bubble. This repetitive explosive boiling activity and interaction of the ultrasound shock waves with the boiling bubbles emulsifies the tissue 108 at the target site 122 to form a liquid-filled lesion, at least partially devoid of cellular structure, with little to no thermal coagulation within the treated region. The reflection of the shock wave from the surface of these millimeter-sized boiling bubbles can also form cavitation bubbles proximate to the boiling bubble that can also induce mechanical damage to tissue.

Mechanical tissue destruction can occur consistently within localized treatment volumes when the temperature of the tissue reaches 100° C. and boiling bubbles form during each pulse or after a series of consecutive pulses. For example, boiling bubbles are generally produced proximate to the focus 120 of the HIFU source 102 (i.e., where shock wave amplitude is the highest). Alternatively, cavitation bubbles can be induced randomly over a larger region. In selected embodiments, for example, the energy deposition of the ultrasound beam can focus within 100 microns of the target site 122. In other embodiments, however, this distance may vary.

In selected embodiments, the pulsing protocol of the HIFU system 100 can be adjusted to control the type of lesion formed in the tissue (e.g., a "liquid" lesion—a completely liquefied mechanical lesion; a "paste" lesion—a partially denatured mechanical lesion; a "thermal" lesion—a thermal lesion with no mechanical damage; or a "boiling" lesion—a thermally denatured lesion with mechanical damage). For example, repeating 10 ms duration shock waves at a pulse repetition frequency that is slow enough (e.g., approximately 2 MHz or 1% duty cycle) to allow cooling between the pulses such that lesion content within the target site 122 and the surrounding tissue 108 shows minimal to no evidence of thermal denaturation. A duty cycle of less than approximately 10% also allows cooling between pulses that minimizes thermal denaturation. In selected embodiments, the duration of the pulses can be reduced over the course of the pulsing protocol to account for a decreasing time to boil caused by the retention of heat in the tissue 108 between pulses. Additionally, the duration of each pulse can be such that the thermally denatured volume of the tissue 108 within each pulse is negligible. For example, in selected embodiments, the duration of each pulse is less than approximately 10 ms. In other embodiments, however, the pulse length can be longer.

In several embodiments, the target site 122 comprises a pressure-release interface within the tissue 108. For example, the target site 122 can include tissue 108 adjacent to an inherent or induced gas or vapor cavity. The gas or vapor cavity can be natural, e.g., gas pockets in the lungs or intestine. Alternately, the bubbles can be created in the tissue 108 by other physical means, including laser ablation or vaporization droplets, e.g., liposomes injected in the vascular system by mild heating. The bubbles can also be introduced by HIFU in the form of cavitation or boiling bubbles in the soft tissue. For example, as discussed above, HIFU has been shown to extracoporeally emulsify regions of bulk tissue by shock wave heating and millisecond boiling, creating bubbles or cavitation bubble clouds. As will be discussed in further detail below with reference to FIGS. 2A-3D, the bubbles or bubble clouds are large enough to act as a pressure-release interface, allowing acoustic atomization and fractioning the tissue into submicron-sized fragments.

The HIFU system 100 can also include systems or devices that detect and monitor tissue ablation initiation and the activity (e.g., heating or bubble activity) in the tissue 108. In some embodiments, for example, these devices can be used during treatment to distinguish boiling bubbles from cavitation bubbles and ensure the pulsing protocol is set to parameters that will induce the desired lesion type. In the embodiment illustrated in FIG. 1, for example, the HIFU source 102 is operably coupled to a voltage probe 110 and an oscilloscope 112 that can monitor and record, respectively, the drive voltage at the HIFU source 102. In other embodiments, however, the HIFU source 102 may be coupled to additional detection and/or monitoring devices.

The HIFU system 100 can also include a passive cavitation detector ("PCD") 124 that monitors acoustic signals associated with tissue ablation. For example, the PCD 124 can include an acoustic receiver (e.g., an ultrasound transducer) separate from the HIFU source 102, but confocally aligned with the focus 120 of the HIFU source 102 such that the PCD 124 can receive real-time acoustic feedback during HIFU treatment. In general, boiling bubbles scatter frequencies that already exist in the incident wave, whereas cavitation bubbles create short pops when they collapse and have a broadband frequency noise. Boiling bubbles may also generate lower frequency noise (e.g., kilohertz frequencies) that can be recorded and used to monitor treatments. As shown in FIG. 1, similar to the voltage probe 110, the PCD 124 can also be coupled to the oscilloscope 112 to record acoustic signals during HIFU treatment.

Echogenic ablation activity and/or the thermal effects of the HIFU treatment can also be monitored using separate devices and systems. The HIFU system 100 illustrated in FIG. 1, for example, includes an imaging system 114 that can create a visual image to monitor the boiling bubbles and thus temperatures of approximately 100° C. in real-time at a depth within the tissue 108. The imaging system 114 can be a separate confocal transducer, an unfocused transducer, another type of confocal or unfocused ultrasound source, one or more sub-element(s) of a multi-element array, and/or a separate imaging system. For example, in one embodiment the imaging system 114 includes an HDI-1000 scanner with a CL 10-5 scanhead made by Philips Medical Systems of Bothell, Wash. In other embodiments, the imaging system 114 can include a magnetic resonance imaging ("MRI") system that can monitor temperature and boiling activity during HIFU treatments or other suitable devices.

In the embodiment shown in FIG. 1, the HIFU system 100 also includes a high-speed camera 116 (e.g., video, still frame) to take video or still images of the target site 122 during HIFU treatment to capture the effects of the HIFU treatment on the tissue 108. Such a camera 116 is generally used with initially transparent tissues or tissue phantoms to capture the thermal effects of HIFU treatment within the tissue 108. Accordingly, the high-speed camera 116 can be especially suited for experiments and testing that include transparent gel phantoms to simulate tissue. The high-speed camera 116 is an optional component that may not be used in some embodiments.

The HIFU system 100 can also simulate the shock waves and heating in water or tissue. Resultant modeling can be used to calculate heating from the shock amplitude of the focal waveform, and for extrapolating pressure waveforms at the focus 120 in water to the equivalent waveforms in tissue. One such method for this extrapolation is called "derating," and is useful for regulatory oversight and HIFU treatment planning. For example, derating can be used to determine values of the acoustic field parameters in the tissue region exposed to HIFU (e.g., the target site 122 and the surrounding tissue 108). During the derating process, low level ultrasound measurements can be taken at the focus 120 in water and scaled to the higher level outputs used during therapeutic HIFU treatments.

The HIFU system 100 can also include a testing apparatus 130 that can assess the extent of mechanical and/or thermal ablation and distinguish among lesion types. In some embodiments, for example, the testing apparatus 130 can send feedback to the function generator 104 or other components of the HIFU system 100 to cause the function generator 104 to select ultrasound parameters designed to achieve a particular type of mechanical or thermal ablation. For example, as will be discussed in further detail below with reference to FIGS. 4A-4D, a user may desire to create a lesion that can be categorized as one of a liquid lesion, a paste lesion, a boiling lesion, or a thermal lesion. The testing apparatus 130 can determine the type of lesion created by the ultrasound source 102 and then automatically instruct the function generator 104 to alter or fine-tune HIFU parameters to better achieve the characteristics of the desired lesion. In further embodiments, the testing apparatus 130 may supply information to a user to allow the user to manually adjust HIFU settings as necessary to achieve the desired lesion type. As will be discussed in further detail below, the testing apparatus 130 can characterize or distinguish ablated tissue at the target site 122 according to at least one of a histological or biochemical trait.

Further details regarding HIFU system components and operating parameters can be found in U.S. patent application Ser. No. 13/085,368, filed Apr. 12, 2011 and entitled "Methods and Systems for Non-Invasive Treatment of Tissue Using High Intensity Focused Ultrasound Therapy," which is hereby incorporated by reference in its entirety.

Figure 2A:
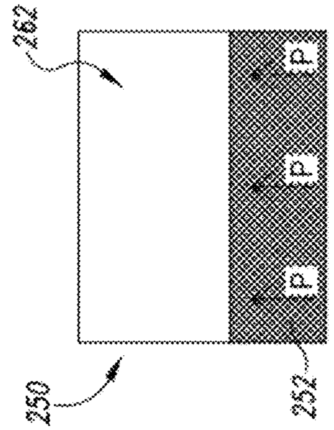
FIGS. 2A-2C are illustrations of planar ultrasound waves modeled at a pressure-release interface in tissue in accordance with several embodiments of the present technology.

FIGS. 2A-3D illustrate various steps of atomizing tissue at pressure-release interfaces using a suitable HIFU system (e.g., the HIFU system 100 of FIG. 1). The techniques for atomizing tissue described below, for example, are directed to particular applications of the HIFU system and associated methods described above. FIGS. 2A-2C, for example, are sequential illustrations of planar waveforms modeled at a pressure-release interface 250 between tissue 252 and a gas or vapor cavity 262 in accordance with several embodiments of the present technology.

Figure 2B:
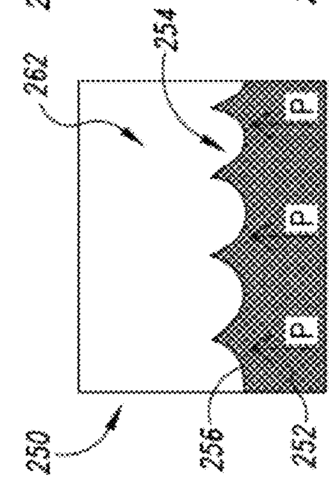
Figure 2C:
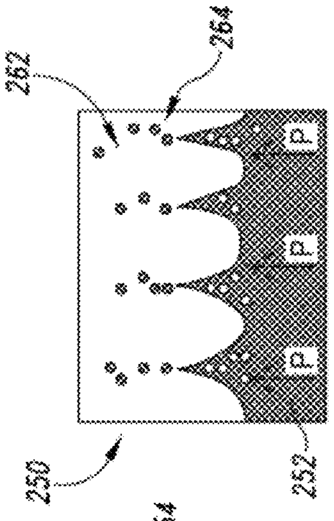

FIG. 2A illustrates the pressure-release interface 250 after the initial application of planar shock waves P. FIG. 2B illustrates the pressure-release interface 250 when capillary waves 254 have been parametrically excited on a surface 256 of the tissue 252. In some embodiments, the capillary waves 254 are excited at half of the ultrasound frequency. FIG. 2C illustrates the pressure-release interface 250 after cavitation and instability of sharp cusps of the capillary waves 254 have caused the emission of droplets or atomization 264 in the tissue 252.

Figure 3A:
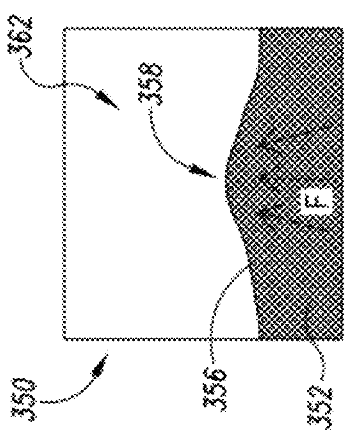
FIGS. 3A-3C are illustrations of focal ultrasound waves modeled at a pressure-release interface in tissue in accordance with several embodiments of the present technology.
Figure 3B:
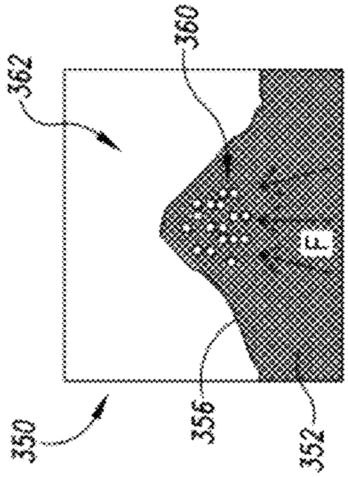
Figure 3C:
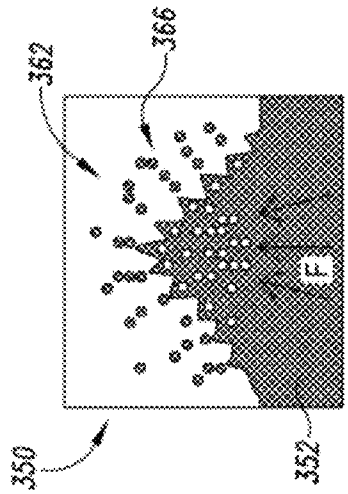
Figure 3D:
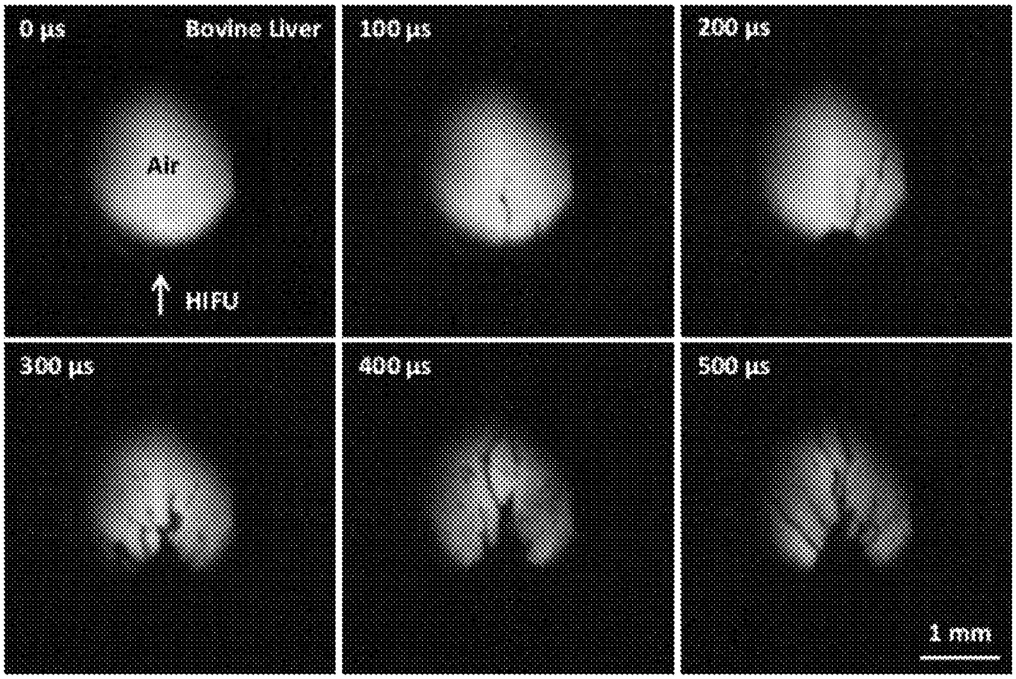
FIG. 3D is a set of photographs of focal ultrasound waves applied to a pressure-release interface in tissue in accordance with several embodiments of the present technology.

FIGS. 3A-3C are sequential illustrations of focal waveforms modeled at a pressure-release interface 350 between tissue 352 and a gas or vapor cavity 362 in accordance with several embodiments of the present technology. FIG. 3A, for example, illustrates the pressure-release interface 350 upon initial application of focused shock waves F. The radiation force from the shock waves F causes a surface 356 of the tissue 352 to become concave at a focal point 358 of the radiation. FIG. 3B illustrates the pressure-release interface 350 after cavitation bubbles 360 have appeared under the surface 356 of the tissue 352. FIG. 3C illustrates the pressure-release interface 350 after cavitation and capillary waves have caused an acoustic fountain and atomization 366 of the tissue 352. The gas or vapor cavity 362 provides the space for the tissue 352 to excite and atomize in this manner. FIG. 3D is a set of photographs of focal ultrasound waves applied to a pressure-release interface in tissue in accordance with several embodiments of the present technology.

Referring to FIGS. 3A-3D together, in some embodiments, the projectiles atomizing from the acoustic fountain 366 can include both fragmented and whole cells and nuclei. In some embodiments, the water content of the tissue 352 can contribute to the degree of tissue erosion. For example, the water content of the tissue 352 can decrease the tissue stiffness and/or the tissue cavitation threshold, thereby increasing the ease of emulsification. Further, water may contribute to tissue emulsification by forming a slurry that is recirculated within the boiling bubble or cavitation bubble cloud. Accordingly, a portion of the tissue 352 can be wetted (e.g., misted with water or a saline solution) prior, during, or after a HIFU treatment. Many types of tissue can exhibit this acoustic fountain effect, including, for example, kidneys, esophageal tissue, skeletal muscle, blood clots, spleen tissue, and/or other suitable tissue.

Figure 4A:
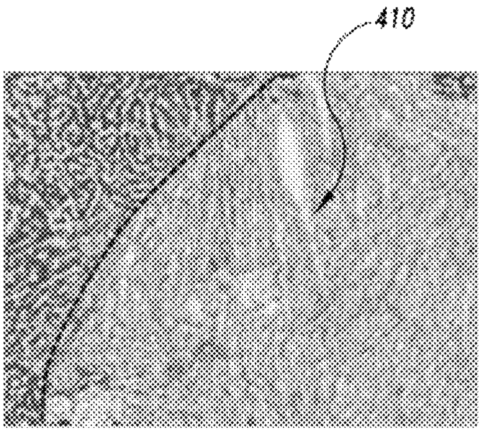
FIGS. 4A-4D are photographs of various types of lesions formed in tissue using HIFU in accordance with embodiments of the present technology.
Figure 4B:
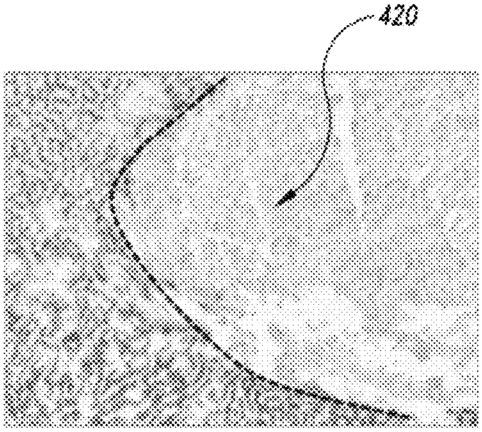
Figure 4C:
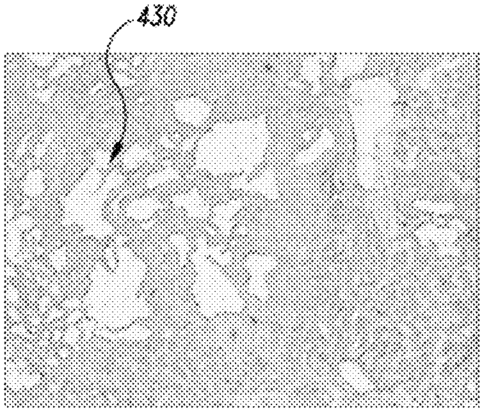
Figure 4D:
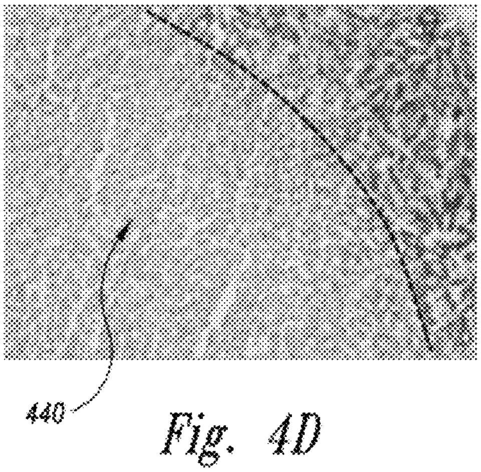

FIGS. 4A-4D are photos of various types of lesions formed in tissue using HIFU in accordance with embodiments of the present technology. The photos are arranged in order of decreasing liquid and increasing thermal components. For example, FIG. 4A illustrates a "liquid" lesion 410, FIG. 4B illustrates a "paste" lesion 420, FIG. 4C illustrates a "boiling" lesion 430, and FIG. 4D illustrates a "thermal" lesion 440. FIGS. 4A, 4B, and 4D include dashed lines to more clearly delineate the ablated and unscathed tissue. For purposes of this disclosure, a liquid lesion 410 is one in which the tissue is nearly or completely emulsified. The lesion 410 includes only mechanical ablation, and no thermal effects. As shown in FIG. 4A, the lesion 410 includes active enzymes in the ablated region. For purposes of this disclosure, a paste lesion 420 can be considered slightly more viscous than a liquid lesion 410, with some non-active enzymes remaining in the lesion 420. For purposes of this disclosure, a boiling lesion 430 includes some pieces of non-emulsified tissue, while a thermal lesion 440 has been at least partially ablated by heat, with a blurrier boundary line between treated and untreated tissue.

A testing method or apparatus, such as testing apparatus 130 described above with reference to FIG. 1, can be used to distinguish among the various types of lesions. In some embodiments, for example, a lesion can be analyzed for microscopic anatomical/structural changes or changes in the quantity or type of cells, molecules, or cellular components. In further embodiments, the testing apparatus can perform biochemical analyses of samples at or around a target site. In some embodiments, a frozen embed of the treatment site can be sectioned and stained to determine cellular structure or contents. In particular embodiments, Haeomatoxylin and Eosin stain and/or nicotinamide adenine dinucleotide diaphorase stain are used to better view changes to the general tissue structure and effects of thermal treatment, respectively. In other embodiments, however, other suitable techniques may be used to test/analyze the treated tissue.

In still further embodiments, the extent of thermal ablation in a lesion can be determined by analyzing the quantity of protein in a lesion sample, as heated proteins denature and become less soluble in water. The contents of the lesion can be removed and a serial salt extraction applied. A Bradford assay or other suitable test can quantify proteins in the sample. In some embodiments, for example, the lesion is characterized as liquid if there is no denatured protein relative to a control sample; as paste if there is approximately 20%-40% denatured protein relative to the control; as boiling if there is approximately 80-85% denatured protein relative to the control; and as thermal if there is approximately 85% or more denatured protein relative to the control. Liquid lesions are purely mechanical lesions, and therefore have not suffered from thermally-induced protein denaturation. In further embodiments, a spectrophotometric determination can distinguish among lesion types.

As discussed above, a HIFU system can be configured to implement pulsing parameters that correspond to a particular, desired type of lesion. The feedback based on the lesion characterization can be used to modify ultrasound parameters. Referring to general histological trends, an increased pulse length, duty cycle, or thermal component will create a more thermal, less liquid lesion (and vice versa) while increasing structural disruption of the tissue will create a more liquid, less thermal lesion. In further embodiments, other desired bioeffects can be induced based on the results of the lesion characterization.

Figure 5:
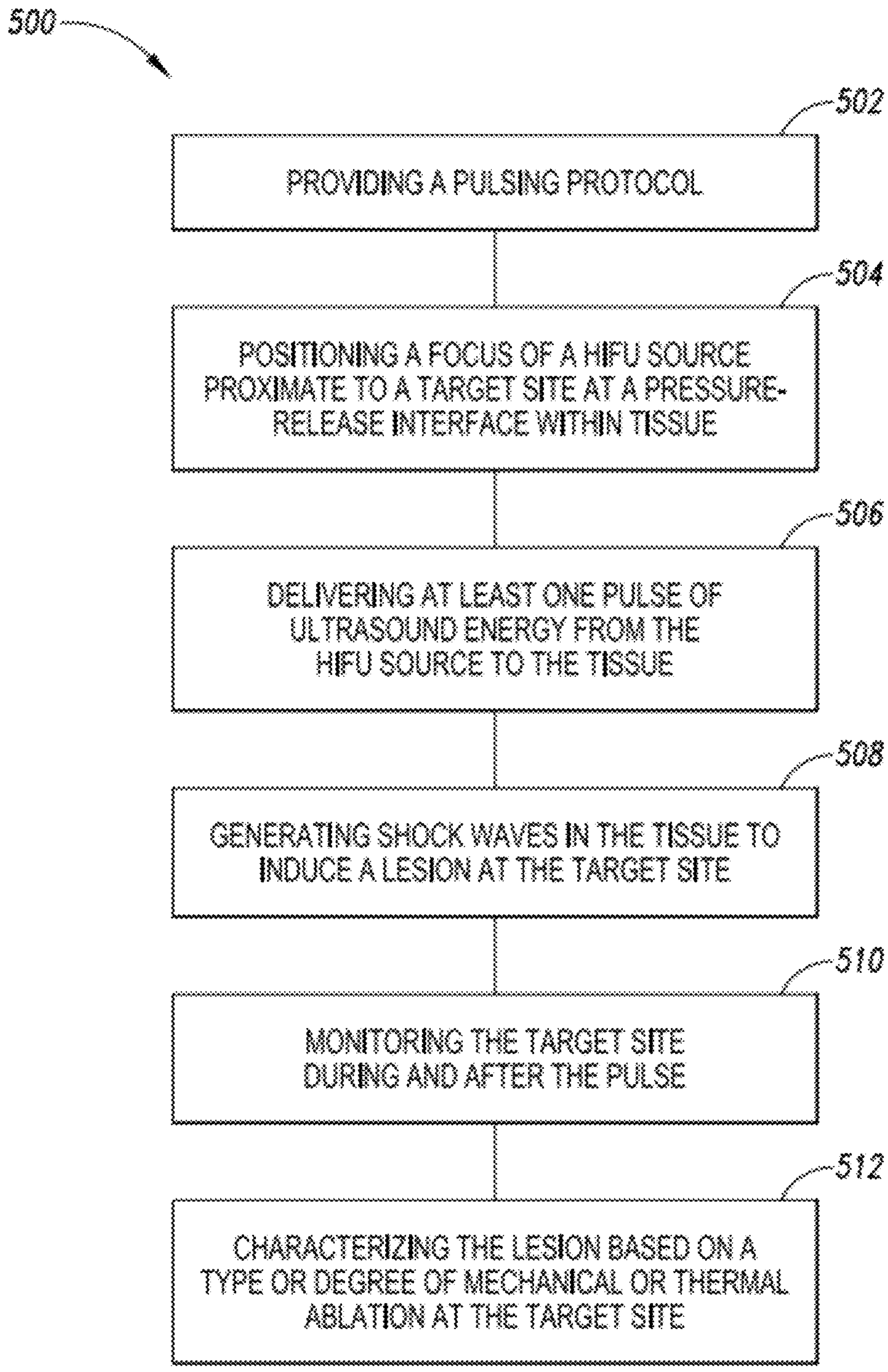
FIG. 5 is a block diagram illustrating a method of treating tissue at a target site in accordance with an embodiment of the present technology.

FIG. 5 is a block diagram illustrating a method 500 of treating tissue at a target site in accordance with an embodiment of the present technology. The method 500 can include providing a pulsing protocol (block 502). As discussed above, a pulsing protocol can take into account the ultrasound frequency at a HIFU source, peak positive pressure at the focus, shock amplitude, pulse length, pulse repetition frequency, and duty cycle. In other embodiments, additional factors related to tissue boiling and shock wave heating can be included in the pulsing protocol. In selected embodiments, a derating process can be used to estimate values of acoustic field parameters of the exposed tissue, and therefrom calculate the requisite peak positive pressures and pulse lengths for shock wave heating and millisecond boiling. The pulsing protocol can also be configured to minimize thermal effects of the HIFU treatment on the tissue. For example, as described above, the duty cycle can be less than 10% to ensure sufficient cooling occurs between shock wave pulses and prevent thermal denature. As another example, the pulse length can be less than approximately 100 ms such that any thermally denatured volume formed within each pulse is negligible. In a particular embodiment, atomization can occur in liver tissue at 60 MPa with individual pulses having a pulse duration of at least 20 μs. When the amplitude is reduced to 15 MPa, atomization can occur when the pulse duration is increased to 10 ms. The pressure threshold can be even lower and reach diagnostic ultrasound levels for a larger number of consecutive pulses or for tissues with less structure. In a particular embodiment, blood clots can atomize at 4 MPa in less than 70 μs and heparinize blood at 2 MPa in less than 70 μs. In several embodiments, the time required to achieve atomization is related to the shock wave amplitude, wherein quicker atomization can correspond to higher amplitudes, and vice versa. The pulsing protocol can be set to take this and other treatment variable relationships into account. Various other pulsing protocols can be established to induce a desired type of lesion as described above.

Once the pulsing protocol is established, the method 500 can continue by positioning a focus of a HIFU source proximate to a target site at a pressure-release interface within tissue (block 504). The pressure-release interface can be similar to the pressure-release interfaces described above with reference to FIGS. 1-3C. For example, the pressure-release interface can include an inherent or induced gas or vapor cavity within tissue. The pressure-release interface can be induced by any of the techniques described above, such as laser ablation, vaporization droplets, injected liposomes, cavitation clouds, etc.

The method 500 can further include delivering at lease one pulse of ultrasound energy from the HIFU source to the tissue (block 506) and generating shock waves in the tissue to induce a lesion at the target site (block 508). In some embodiments, each pulse of shock waves at the target site can generate boiling bubbles within milliseconds. This rapid millisecond boiling can mechanically disrupt the tissue without evident thermal damage. Additionally, as described above, the HIFU source can deliver shock waves to its focus to consistently induce boiling within a localized treatment area or can be planar to induce boiling over a larger area of tissue. Therefore, the millisecond boiling provided by this HIFU method 200 provides a repeatable, directable, and predictable mechanical destruction of tissue to produce a desired type of lesion. Alternatively, thermal treatment can be applied. Optionally, the target site can be monitored during HIFU treatment to ensure boiling and/or otherwise observe the effects of the HIFU treatment (block 210).

The method 500 can also include characterizing the lesion based on a type or degree of mechanical or thermal ablation at the target site (block 512). As described above, histological and/or biochemical testing or observation can be performed to distinguish or categorize among lesion types. Based on the characterization, feedback can be sent to alter or fine-tune the pulsing protocol to achieve a desired type of lesion.

From the foregoing, it will be appreciated that specific embodiments of the technology have been described herein for purposes of illustration, but that various modifications may be made without deviating from the disclosure. For example, the HIFU system 100 of FIG. 1 can include additional devices and/or systems to facilitate shock wave heating of the tissue 108. For example, the HIFU system 100 can include a timing board to trigger the function generator 104, additional amplifiers 106, high-pass or other suitable filters, a computer to drive the entire HIFU system 100, and/or other suitable devices related to HIFU treatments. Additional assays, stains, or alternate testing devices or methods can be used to characterize lesions. Certain aspects of the new technology described in the context of particular embodiments may be combined or eliminated in other embodiments. For example, the HIFU system 100 does not need to include some of the devices shown in FIG. 1. In selected embodiments, the HIFU system can include only one of or a combination of the voltage probe 110, the PCD 124, the imaging system 114, and/or the high-speed camera 116 to monitor the thermal and mechanical effects of the HIFU treatment. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A method of non-invasively treating tissue, the method comprising:

pulsing ultrasound energy from an ultrasound source to a target site in tissue, wherein the ultrasound source is configured to emit high intensity focused ultrasound (HIFU) waves, and wherein the target site comprises a pressure-release interface located between tissue and a gas or vapor cavity;

generating shock waves in the tissue to induce a lesion in the tissue at the target site;

atomizing the tissue at the pressure-release interface to create an acoustic fountain; and characterizing the lesion based, at least in part, on a degree of at least one of a mechanical or thermal ablation of the tissue at the target site.

2. The method of claim 1 wherein characterizing the lesion based on a degree of at least one of a mechanical or thermal ablation of the tissue comprises characterizing the lesion based on a change of at least one of a cellular structure, molecular structure, protein structure, protein quantity, protein solubility, or cellular quantity at the target site.

3. The method of claim 1 wherein characterizing the lesion based on a degree of at least one of a mechanical or thermal ablation of the lesion comprises using at least one of a Haematoxylin and Eosin stain or a nicotinamide adenine dinucleotide diaphorase stain to characterize the lesion.

4. The method of claim 1 wherein characterizing the lesion based on a degree of at least one of a mechanical or thermal ablation of the tissue comprises using at least one of a serial salt extraction, protein-quantifying assay, or spectrophotometric determination to characterize the lesion.

5. The method of claim 1 wherein characterizing the lesion based on a degree of at least one of a mechanical or thermal ablation of the tissue comprises characterizing the lesion as a liquid lesion, a paste lesion, a boiling lesion, or a thermal lesion.

6. The method of claim 1 wherein the target site comprises a naturally-occurring gas or vapor cavity located within the tissue.

7. The method of claim 1, further comprising wetting the pressure-release interface of the gas or vapor cavity located within the tissue.

8. The method of claim 1 wherein generating shock waves in the tissue comprises generating planar waves in the tissue.

9. The method of claim 1 wherein generating shock waves in the tissue to induce a lesion in the tissue at the target site comprises generating a focused beam of waves in the tissue to create the acoustic fountain and atomize the tissue at the target site.

10. The method of claim 1 wherein:

pulsing ultrasound energy comprises pulsing ultrasound energy to the pressure-release interface at a pulse length comprising multiple cycles of the ultrasound wave; and generating shock waves in the tissue comprises generating shock waves having amplitudes between 10 MPa and 80 MPa.

11. The method of claim 1, further comprising selecting a setting of the ultrasound source corresponding to a desired mechanical or thermal phase of the lesion.

12. The method of claim 1, further comprising establishing a pulsing protocol taking into account factors comprising ultrasound frequency of the ultrasound source, pulse length, pulse repetition frequency, and duty cycle.

13. The method of claim 1 wherein generating shock waves in the tissue comprises generating shock waves such that a surface of the tissue becomes concave.

14. The method of claim 1, further comprising creating the pressure-release interface of the gas or vapor cavity located within the tissue by introducing or inducing a gas or vapor at the target site.

15. The method of claim 14 wherein inducing a gas or vapor at the target site comprises inducing cavitation bubbles or boiling bubbles in the tissue with HIFU.

* * * * *

UNITED STATES PATENT AND TRADEMARK OFFICE

CERTIFICATE OF CORRECTION

PATENT NO. : 9,498,651 B2
APPLICATION NO. : 13/444466
DATED : November 22, 2016
INVENTOR(S) : Oleg A. Sapozhnikov et al.

It is certified that error appears in the above-identified patent and that said Letters Patent is hereby corrected as shown below:

In the Specification

In Column 4, Line 44, delete “extracoporeally” and insert -- extracorporeally --, therefor.

In Column 7, Line 37, delete “Haeomatoxylin” and insert -- Haematoxylin --, therefor.

In Column 8, Line 52, delete “lease” and insert -- least --, therefor.

Signed and Sealed this
Seventeenth Day of October, 2017

Joseph Matal

Joseph Matal
*Performing the Functions and Duties of the*
*Under Secretary of Commerce for Intellectual Property and*
*Director of the United States Patent and Trademark Office*